United States Patent
Montgomery et al.

(10) Patent No.: US 9,522,261 B2
(45) Date of Patent: Dec. 20, 2016

(54) METHOD AND APPARATUS FOR PROVIDING HYDRATION FLUID

(75) Inventors: Hugh E Montgomery, Solihull (GB);
Michael Mythen, Ealing (GB);
Anthony Thorne, Abingdon (GB)

(73) Assignees: Hugh E Montgomery, London (GB);
Michael Mythen, Ealing (GB)

( * ) Notice: Subject to any disclaimer, the term of this patent is extended or adjusted under 35 U.S.C. 154(b) by 1185 days.

(21) Appl. No.: 13/574,375

(22) PCT Filed: Jan. 21, 2011

(86) PCT No.: PCT/GB2011/000077
§ 371 (c)(1),
(2), (4) Date: Nov. 13, 2012

(87) PCT Pub. No.: WO2011/089394
PCT Pub. Date: Jul. 28, 2011

(65) Prior Publication Data
US 2013/0150823 A1  Jun. 13, 2013

(30) Foreign Application Priority Data

Jan. 22, 2010 (GB) .................................. 1001069.2

(51) Int. Cl.
*A61M 37/00* (2006.01)
*A61M 5/168* (2006.01)
(Continued)

(52) U.S. Cl.
CPC ......... *A61M 37/00* (2013.01); *A61M 5/14232* (2013.01); *A61M 5/16877* (2013.01);
(Continued)

(58) Field of Classification Search
CPC .. A61M 37/00; A61M 5/142; A61M 5/14232;
A61M 5/1407; A61M 5/1408; A61M 5/14; A61M 5/16827; A61M 5/16895; A61M 5/172; A61J 7/0409; A61J 7/0418
See application file for complete search history.

(56) References Cited

U.S. PATENT DOCUMENTS

| 2,700,384 A | 1/1955 | Ivory |
| 4,276,999 A | 7/1981 | Reichenberger |

(Continued)

FOREIGN PATENT DOCUMENTS

| EP | 0349261 A1 | 1/1990 |
| EP | 0908395 A1 | 4/1999 |

(Continued)

OTHER PUBLICATIONS

Office Action issued for Japanese Pat. Appl. No. 2012-549411, dated Nov. 25, 2014, 2 pp.

(Continued)

*Primary Examiner* — Imani Hayman
*Assistant Examiner* — Nilay Shah
(74) *Attorney, Agent, or Firm* — Bell & Manning, LLC

(57) ABSTRACT

The invention relates to a method and apparatus for providing hydration fluids. The invention allows for a 'background' rate of providing a hydration fluid to be automatically supplied by an apparatus to a patient, for example intravenously, and for the patient to receive an extra amount of hydration fluid, or 'bolus dose', to be provided when the patient sends a signal to the apparatus. In preferred embodiments the background supply rate, the volume and rate of supply of the bolus dose and the maximum extra volume that can be provided as bolus doses in a given time can be set, for example, by a nurse.

18 Claims, 5 Drawing Sheets

(51) Int. Cl.
*A61M 5/172* (2006.01)
*A61J 7/04* (2006.01)
*A61M 5/14* (2006.01)
*A61M 5/142* (2006.01)
*A61J 1/20* (2006.01)
*A61J 1/22* (2006.01)

(52) U.S. Cl.
CPC ...... *A61M 5/16895* (2013.01); *A61M 5/1723* (2013.01); *A61J 1/20* (2013.01); *A61J 1/22* (2013.01); *A61J 7/0409* (2013.01); *A61J 7/0418* (2015.05); *A61J 2200/30* (2013.01); *A61J 2200/74* (2013.01); *A61M 5/142* (2013.01); *A61M 5/1407* (2013.01)

(56) References Cited

U.S. PATENT DOCUMENTS

| | | | |
|---|---|---|---|
| 4,435,173 A * | 3/1984 | Siposs | A61M 5/1456 128/DIG. 1 |
| 4,443,218 A * | 4/1984 | DeCant, Jr. | A61M 5/14276 128/DIG. 12 |
| 4,475,666 A | 10/1984 | Bilbrey et al. | |
| 4,496,351 A | 1/1985 | Hillel et al. | |
| 4,670,007 A | 6/1987 | Wheeldon et al. | |
| 4,798,590 A | 1/1989 | O'Leary et al. | |
| 4,957,226 A | 9/1990 | Pacia | |
| 4,966,580 A | 10/1990 | Turner et al. | |
| 5,011,477 A | 4/1991 | Winchell | |
| 5,061,243 A | 10/1991 | Winchell et al. | |
| 5,084,828 A | 1/1992 | Kaufman et al. | |
| 5,224,934 A | 7/1993 | Payne et al. | |
| 5,603,436 A | 2/1997 | Leoncavallo | |
| 6,145,707 A | 11/2000 | Baudin | |
| 6,286,733 B1 | 9/2001 | Francois | |
| 6,398,073 B1 | 6/2002 | Nicolle | |
| 6,416,495 B1 | 7/2002 | Kriesel | |
| 7,232,420 B1 | 6/2007 | Abulhaj | |
| 2001/0051788 A1 | 12/2001 | Paukovits et al. | |
| 2003/0048185 A1 | 3/2003 | Citrenbaum et al. | |
| 2003/0140928 A1 | 7/2003 | Bui et al. | |
| 2003/0160063 A1 | 8/2003 | Paukovits et al. | |
| 2004/0055254 A1 | 3/2004 | Setton | |
| 2004/0215155 A1 | 10/2004 | Wolfe | |
| 2005/0020996 A1 | 1/2005 | Hartlaub | |
| 2005/0187515 A1 | 8/2005 | Varrichio | |
| 2006/0049372 A1 | 3/2006 | Lien | |
| 2006/0235353 A1 | 10/2006 | Gelfand | |
| 2006/0270971 A1 | 11/2006 | Gelfand et al. | |
| 2007/0088333 A1 * | 4/2007 | Levin | A61B 5/14507 604/890.1 |
| 2008/0091142 A1 | 4/2008 | Trombley | |
| 2008/0221512 A1 * | 9/2008 | Da Silva | A61B 5/20 604/65 |
| 2009/0076462 A1 | 3/2009 | Kiani | |
| 2010/0081942 A1 | 4/2010 | Huiku | |
| 2010/0265072 A1 | 10/2010 | Goetz et al. | |

FOREIGN PATENT DOCUMENTS

| | | | |
|---|---|---|---|
| GB | 2202449 A * | 9/1988 | A61J 9/00 |
| GB | 2391223 A | 2/2004 | |
| JP | 11314651 A | 11/1999 | |
| JP | 2001-503302 | 3/2001 | |
| JP | 2008-512179 | 4/2008 | |
| JP | 2009-506872 | 2/2009 | |
| JP | 2009-54183 | 3/2009 | |
| WO | WO98/19647 | 5/1998 | |
| WO | WO 98/19647 A1 | 5/1998 | |
| WO | WO 02/100320 A1 | 12/2002 | |
| WO | WO03/092769 | 11/2003 | |
| WO | WO 03/105931 A1 | 12/2003 | |
| WO | WO 2005/022058 A2 | 3/2005 | |
| WO | WO2006/031249 | 3/2006 | |
| WO | WO2007/030403 | 3/2007 | |
| WO | WO 2008/020767 A1 | 2/2008 | |
| WO | WO 2009/007969 | 1/2009 | |

OTHER PUBLICATIONS

International Search Report and Written Opinion received in PCT/GB2011/000077, Aug. 11, 2011.
Search Report received in GB0815510.3, Date of search Oct. 8, 2008.
Search Report received in GB0815509.5, Date of search Nov. 18, 2008.
Search Report received in GB0815510.3, Date of search Feb. 20, 2009.
Search Report received in GB1001069.2, Date of search Jun. 9, 2010.
Search Report received in GB1001069.2, Date of search Nov. 11, 2010.
International Search Report issued in PCT/GB2012/051826, Nov. 20, 2012.

* cited by examiner

METHOD AND APPARATUS FOR PROVIDING HYDRATION FLUID

This application is a National Stage Entry of International Application No. PCT/GB2011/000077, filed Jan. 21, 2011, which claims the benefit of GB Patent Application No. 1001069.2, filed Jan. 22, 2010, the contents of which are herein incorporated by reference in their entirety.

This invention is related to the provision of hydration fluids. In particular, the invention relates to an apparatus, and associated method, for providing hydration fluids in response to a signal from a user.

Each year, 3 million operations are performed in the UK, with a further 30 million in mainland Europe. In first world countries overall, the number exceeds 100 million. In England alone, there are nearly 160,000 patients in National Health Service (NHS) residential/acute/general hospital beds in any given hour. In addition, 42 NHS palliative care institutions offer 5 million inpatient days/year—a number dwarfed by those provided by hospices. The numbers for the European Union and USA are correspondingly vastly higher in all categories.

For these individuals, the importance of appropriate hydration should not be underestimated, not only for patient comfort, but for survival. Many patients are unable or unwilling to drink and for these, intravenous fluid therapy is required.

Prescribing the appropriate volumes of fluid (and rate of administration) can prove very difficult. In practice, the task is often left to relatively inexperienced individuals. Further, decisions are infrequently reviewed (often less than once per day), and such revised regimens are often based on scant (or absent) data and inappropriate (generally inadequate) prescribing can have profound and detrimental consequences: even modest fluid depletion decreases well-being, making it harder to cope with other symptoms, and impairs kidney function, and overall surgical outcome. Even quite small volumes of additional fluid administered in the peri-operative period improve outcome in terms of complication rates, durations of hospital stay, and even mortality.

Therefore, there is a problem that the existing methods of providing hydration fluids are unreliable and do not meet patients' needs. Patients who do not receive enough fluids become uncomfortable and dehydrated. If they are unable to move, their only option is to call a nurse. The increased attention needed from nurses requires increased manpower and resources on the ward, which leads to increased costs. Further, such reliance on nurses can be humiliating or embarrassing for the patients themselves.

There is also a further problem associated with patients who are nil-by-mouth. Such patients have their intake of food and fluids restricted, for example before an invasive operation. However, nil-by-mouth patients can often become extremely thirsty, even if they are being provided with intravenous fluids to compensate for the prohibition on oral ingestion of fluids. This thirst can lead to the patient becoming uncomfortable. Therefore, there is a problem associated with how to improve the patient comfort whilst maintaining their nil-by-mouth status.

According to a first aspect of the invention there is provided a method for dispensing hydration fluid, the method comprising: in response to a signal from a user, dispensing a predetermined metered amount of hydration fluid for oral ingestion, wherein the predetermined metered amount of hydration fluid for oral ingestion is not more than 20 ml.

This method allows a patient to request a small amount of hydration fluid, which can then be dispensed automatically for drinking and for wetting the patient's mouth. Dispensing small amounts of fluid is particularly advantageous for patients who are unable to sit up to drink normally. In that case, dispensing a large amount of fluid is potentially dangerous, as the patient may choke. In contrast, by dispensing a small amount of fluid the patient is easily able to drink, and is able to control their state of hydration even if they are relatively infirm. Further, dispensing a small amount of hydration fluid for oral ingestion is preferable for patients who are nil-by-mouth. In that case, the patient may be thirsty and dispensing a small amount of fluid will wet their mouth and relieve their thirst, without compromising their nil-by-mouth status. Preferably, the predetermined metered amount of hydration fluid for oral ingestion is not more than 10 ml and is more preferably not more than 5 ml.

According to a second aspect of the invention, there is provided a method for dispensing hydration fluid, the method comprising: in response to a signal from a user, determining if first dispensing criteria are met, the first dispensing criteria being based on a dispensing history of a hydration fluid for oral ingestion, and if it is determined that the first dispensing criteria are met, dispensing a predetermined metered amount of hydration fluid for oral ingestion.

This method allows for a patient to receive hydration fluid on demand, as long as dispensing criteria have been met. It is desirable for a patient to be able to administer their own hydration, as this improves their overall comfort and can accelerate patient recovery after operation. However, it is also desirable to monitor a patient's fluid intake and to ensure that a patient does not drink too much. Therefore, the method of the present aspect allows for a patient to control their hydration and to be provided with hydration fluids automatically, whilst predetermined dispensing criteria ensure that a patient does not receive too much fluid.

Preferably, determining if the first dispensing criteria are met further comprises determining how many times the predetermined metered amount of hydration fluid for oral ingestion has been dispensed in a first predetermined period, and the first dispensing criteria are deemed met if it is determined that the number of times the hydration fluid for oral ingestion has been dispensed in the first predetermined period is less than a first predetermined number of times.

In this case, the dispensing criteria are based upon the dispensing history of the hydration fluid for oral ingestion. This allows for hydration fluid to be dispensed if, for example, no hydration fluid has been dispensed for a long time. In contrast if the hydration fluid has been dispensed several times recently, further hydration fluid may not be dispensed to prevent the patient receiving too much fluid.

Preferably, the predetermined metered amount of hydration fluid for oral ingestion is not more than 20 ml, and is preferably not more than 10 ml and is more preferably not more than 5 ml. As mentioned above, dispensing small amounts of hydration fluid is particularly advantageous for patients who cannot sit up, or are nil-by-mouth.

Preferably, the first predetermined period is in the range of from 30 to 90 minutes, preferably from 45 to 75 minutes and more preferably is from 55 to 65 minutes. Also, the first predetermined number of times is in the range of from 4 to 12, more preferably from 6 to 10 and still more preferably from 7 to 9. These parameters ensure that a patient only receives a suitable amount of fluid.

Preferably, the method further comprises: in response to said signal from said user, determining if second dispensing criteria are met, the second dispensing criteria being based on a dispensing history of a hydration fluid for intravenous delivery, and if it is determined that the second dispensing criteria are met, the method further comprises dispensing a predetermined metered amount of hydration fluid for intravenous delivery.

This embodiment allows for the dispensing of both hydration fluid for intravenous delivery and hydration fluid for oral delivery. The combined provision of these two forms of hydration fluid can be particularly effective for improving both the overall level of hydration in a patient and also the patient's comfort. Intravenous delivery of hydration fluid ensures that the hydration level of a patient is quickly improved, whilst oral delivery of hydration fluid improves patient comfort by wetting the patient's mouth.

Preferably, determining if the second dispensing criteria are met further comprises determining how many times the predetermined metered amount of hydration fluid for intravenous delivery has been dispensed in a second predetermined period, and the second dispensing criteria are met if it is determined that the number of times the hydration fluid for intravenous delivery has been dispensed in the second predetermined period is less than a second predetermined number of times. This ensures that the dispensing of the hydration fluid for intravenous delivery is conditional upon the dispensing history of the hydration fluid for intravenous delivery. This prevents too much hydration fluid for intravenous delivery being dispensed.

Preferably, the predetermined metered amount of hydration fluid for intravenous delivery is in the range of from 10 to 1000 ml, preferably from 10 to 500 ml, and more preferably from 100 to 300 ml. Also, the second predetermined period is in the range of from 30 to 90 minutes, preferably from 45 to 75 minutes and more preferably is from 55 to 65 minutes. Also, the second predetermined number of times is in the range of from 1 to 5, more preferably from 1 to 3 and still more preferably is 2. These parameters ensure that the patient does not receive too much hydration fluid for intravenous delivery. Also, the predetermined metered amount of hydration fluid for intravenous delivery is dispensed at a flow rate in the range of from 1 to 4000 ml/hr, preferably from 1000 to 3000 ml/hr and more preferably from 1500 to 2500 ml/hr.

Preferably, the method further comprises determining if the first dispensing criteria are met further comprises determining the length of time since a predetermined metered amount of hydration fluid for oral ingestion was dispensed, and wherein the first dispensing criteria are not met if the determined length of time is less than a predefined length of time.

Preferably, the method further comprises determining if the first dispensing criteria are met further comprises determining the total amount of fluid dispensed in a third predetermined period, and wherein the first dispensing criteria are not met if the total amount of fluid dispensed in the third predetermined period is greater than a predetermined amount of fluid.

Preferably, the method further comprises dispensing a background flow rate of hydration fluid for intravenous delivery. This allows a continuous provision of hydration fluid to the patient, which in turn helps maintain a steady level of hydration.

According to a third aspect of the present invention, there is provided a method comprising: dispensing a background flow of hydration fluid for intravenous delivery, and in response to a signal from a user, dispensing a predetermined metered amount of hydration fluid for oral ingestion.

This method provides a continuous background flow of hydration fluid to the patient, helping to maintain a steady level of hydration. Nonetheless, the patient may start to feel dehydrated or thirsty. Therefore, the method provides for further hydration fluid to be dispensed orally, thus wetting the patient's mouth and improving the overall level of comfort of the patient.

Preferably, the background flow of hydration fluid for intravenous delivery is in the range of from 0 to 1500 ml/hr, preferably from 0 to 1000 ml/hr and more preferably from 500 to 1000 ml/hr. The background flow rates are suitable for maintaining a steady level of hydration in a patient.

In all embodiments, the fluid for intravenous delivery is preferably dispensed to the user. This provides the user with control over their level of hydration. Preferably, the hydration fluid for oral ingestion is dispensed to the user's mouth through a tube. This is a convenient way of providing hydration fluid for oral ingestion.

According to a fourth aspect, the invention provides a method for dispensing hydration fluid, the method comprising: in response to a signal from a user, dispensing a predetermined metered amount of hydration fluid for oral ingestion, wherein the signal from the user is provided via a switch forming part of a mouth assembly, and the hydration fluid for oral ingestion is dispensed through the mouth assembly.

According to this aspect, the patient is able to signal for hydration fluid by using a switch in a mouth assembly. This is a convenient location for providing the switch, because the patient is often provided with a mouth assembly in order to receive the hydration fluid for oral ingestion.

Preferably, the switch is mouth operable and more preferably the switch is a pressure switch. In this case, the mouth assembly can be considered to be an "automatic" or "electronic" drinking straw. If the pressure switch is configured to signal when the user sucks through the mouth assembly, then the hydration fluid is dispensed when the user sucks. This design provides an apparatus which is intuitive for a user to operate to obtain hydration fluid, especially for infirm patients.

According to a fifth aspect, the present invention provides a method for monitoring a hydration fluid dispensing process, the method comprising: determining the rate at which hydration fluid is leaving a reservoir, comparing said determined rate to a stored desired flow rate; providing a signal indicative of whether the stored desired rate is the same as the determined rate at which hydration fluid is leaving the reservoir, based on said comparing.

This method allows for the detection of a situation in which the desired flow rate is not the same as the actual flow rate from a reservoir. This may occur, for instance, if a tube through a peristaltic pump becomes blocked. Alternatively, this may occur when a feed tube works itself free of the pump—leading to a situation in which fluid is free to flow from the reservoir without impediment—a situation known as "free-flow". In either case, it is desirable to notice that the desired flow rate is not being provided as quickly as possible. Therefore, the method provides a signal which indicates whether the desired flow rate is being provided. The signal may be an audible or visual alarm, which may either begin or cease when it is determined that the rates are different. Preferably, the method further comprises sounding an alarm, when said signal is indicative that the stored desired rate is not the same as the determined rate.

Preferably, the reservoir is provided on a load cell, and the step of determining the actual rate further comprises: determining the rate of change mass measured by the load cell.

Measuring the rate of change of mass of the reservoir is a preferable way of determining the actual flow rate of fluid out of the reservoir because this is non-invasive to the hydration fluid flow path. It does not require providing any further flow meters or any other devices in contact with the fluid, and therefore reduces the risk of any contamination or fault with the equipment for providing the hydration fluid.

According to another aspect, the invention provides an apparatus for dispensing hydration fluid, the apparatus comprising: a signal input device for receiving a signal from a user, the apparatus being configured such that, in response to the signal input device receiving a signal from the user, a predetermined metered amount of hydration fluid for oral ingestion is dispensed, wherein the predetermined metered amount of hydration fluid for oral ingestion is not more than 20 ml.

According to another aspect, the invention provides an apparatus for dispensing hydration fluid, the apparatus comprising: a signal input device for receiving a signal from a user, a control unit configured to determine, in response to the signal input device receiving a signal from the user, if first dispensing criteria are met, the first dispensing criteria being based on a dispensing history of a hydration fluid for oral ingestion, and the apparatus being configured such that a predetermined metered amount of hydration fluid for oral ingestion is dispensed if it is determined by the control unit that the first dispensing criteria are met.

According to another aspect, the invention provides an apparatus for dispensing hydration fluid, the apparatus being configured to dispense a background flow of hydration fluid for intravenous delivery, the apparatus further comprising: a signal input device for receiving a signal from a user, the apparatus being further configured such that, in response to the signal input device receiving a signal from the user, a predetermined metered amount of hydration fluid for oral ingestion is dispensed.

According to another aspect, the invention provides an apparatus for dispensing hydration fluid, the apparatus comprising: a mouth assembly comprising a switch, operable by a user to send a signal, a signal input device for receiving the signal from a user, the apparatus being further configured such that, in response to the signal input device receiving the signal sent from the switch by the user, a predetermined metered amount of hydration fluid for oral ingestion is dispensed through the mouth assembly.

According to another aspect the invention provides an apparatus for monitoring a hydration fluid dispensing process, the apparatus comprising: a memory configured to store a desired flow rate, and a control unit configured to determine the rate at which hydration fluid is leaving a reservoir, and to compare the determined flow rate to the stored desired flow rate, wherein the apparatus is configured to provide a signal indicative of whether the stored desired rate is the same as the rate at which fluid is leaving the reservoir.

The invention is described below, by way of non-limitative example only, with reference to the accompanying drawings, in which.

Figure 1:
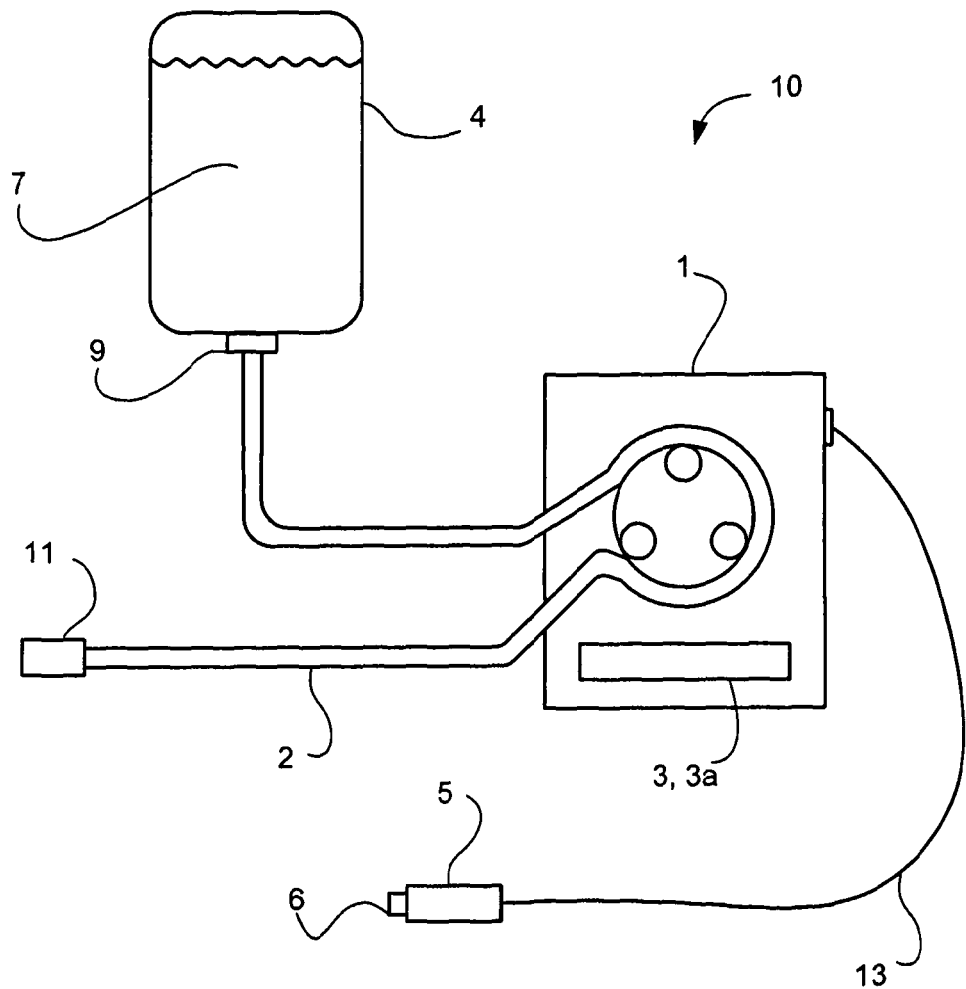
FIG. 1 is a diagram of a system for providing hydration fluids in accordance with the first embodiment of the invention.

FIG. 1 shows a system 10 for providing hydration fluid for oral ingestion 7 in accordance with a first embodiment of the invention. The hydration fluid for oral ingestion 7 itself can be any fluid suitable for hydrating that may be orally ingested, such as water, or a high calorie fluid or a nutritionally enriched fluid.

The system 10 comprises a reservoir 4, containing the hydration fluid for oral ingestion 7. Preferably, the reservoir holds at least 250 ml of hydration fluid for oral ingestion 7, more preferably holds at least 500 ml of hydration fluid for oral ingestion 7, still more preferably holds at least 1 liter of hydration fluid for oral ingestion 7 and even more preferably holds at least 3 liters of hydration fluid for oral ingestion 7. The reservoir 4 itself is preferably a bag or pouch constructed from a collapsible material, e.g. a polymer. The reservoir 4 is also preferably transparent, so that the hydration fluid for oral ingestion 7 may be observed in the reservoir 4. The reservoir 4 may also be provided with gradations to indicate the amount of fluid remaining in the reservoir 4 or the amount of hydration fluid for oral ingestion 7 that has been emptied from the reservoir 4.

Preferably, the reservoir 4 is a pre-filled and/or pre-sealed unit, containing a sterile hydration fluid for oral ingestion 7. Such pre-filled and pre-sealed reservoirs 4 are preferably provided in a sterile packaging, to ensure that the reservoir 4 itself is also sterile. However, in other embodiments the reservoir may be re-usable and re-fillable.

The reservoir 4 is attached to a tube 2 by any suitable means. In one embodiment, the tube 2 is connected to the reservoir 4 via a connection 9. The tube 2 may be integrally attached to the reservoir 4, or may be detachable. In the case of a detachable connection 9, any suitable detachable connection may be used. Examples of possible detachable connections 9 include a screw connection, luer lock or a spear connection which punctures the reservoir 4.

The end of the tube 2 not connected to the reservoir 4 is connected to a mouth piece 11. The mouth piece may take any form suitable for delivering hydration fluid for oral ingestion 7 from the tube 2 to the mouth of a user. In one embodiment, the mouth piece 11 may take the form of a straw or drinking tube. Such a mouth piece 11 may be preferable for users who have a good range of movement and motor control. In other embodiments, the mouth piece 11 may take a form which is designed to be permanently positioned to provide hydration fluid to the user's gut. This includes the use of nasogastric, nasojejunal or percutaneous enterostomy tubes. Such designs of mouth piece 11 may be preferable for users with limited movement and motor control.

The system 10 includes a means for providing fluid for oral ingestion 7 from the reservoir 4 through the tube 2 at a controlled rate. In a preferred embodiment, as depicted in FIG. 1, the means for providing hydration fluid for oral ingestion is a peristaltic pump 1 which forces hydration fluid for oral ingestion 7 through a tube 2 using rollers to squeeze and release the tube 2. However, any suitable means for providing hydration fluid for oral ingestion 7 can be used, such as a drip counter and controlled clamp or a different type of pump. Due to the volumes of hydration fluid for oral ingestion 7 stored in the reservoir 4, a syringe pump is not a preferred embodiment of the means for providing hydration fluid for oral ingestion 7, and according to one aspect of the invention a syringe pump is not used as a means for providing the hydration fluid for oral ingestion 7.

The system 10 further comprises a user-manipulable signal input means 5 for sending a signal to the means for providing fluid. The means for providing fluid is arranged to detect the signals from the signal input means 5. In one embodiment, as shown in FIG. 1, the signal input means 5 comprises a hand-held device with a button 6, which can be pressed by a patient. The signal input means 5 is shown in FIG. 1 as connected to the pump 1 via a wire 13. However, any suitable means of connection between the signal input means 5 and the means for providing fluid may be used such as methods of wireless communication. Preferably, the button 6 is provided on a unit which is easy to hold. To ensure the signal input means 5 can be used even by a relatively infirm patient, it should not be difficult to operate. The force required to press the button 6 should preferably be at least high enough to avoid the button being operated by being accidentally knocked, but low enough to allow weaker patients to operate the button 6.

The pump 1 of FIG. 1 has a control unit 3. In FIG. 1 the control unit is within pump 1, but the control unit 3 may be a separate device to the pump 1. The control unit 3 can be used, by a person other than the patient, for example the doctor or nurse, to set how the pump 1 responds to receiving a signal from the signal input means 5. As such, the control unit 3 may incorporate some form of control panel 3a, as shown in FIG. 1. The control panel 3a is preferably secured either physically (e.g with a protective cover and/or a key) or by a password to prevent unauthorised persons (including the patient) using the control panel 3a to modify the settings of the pump 1. Alternatively, the control unit 3 may be programmable remotely.

Figure 2:
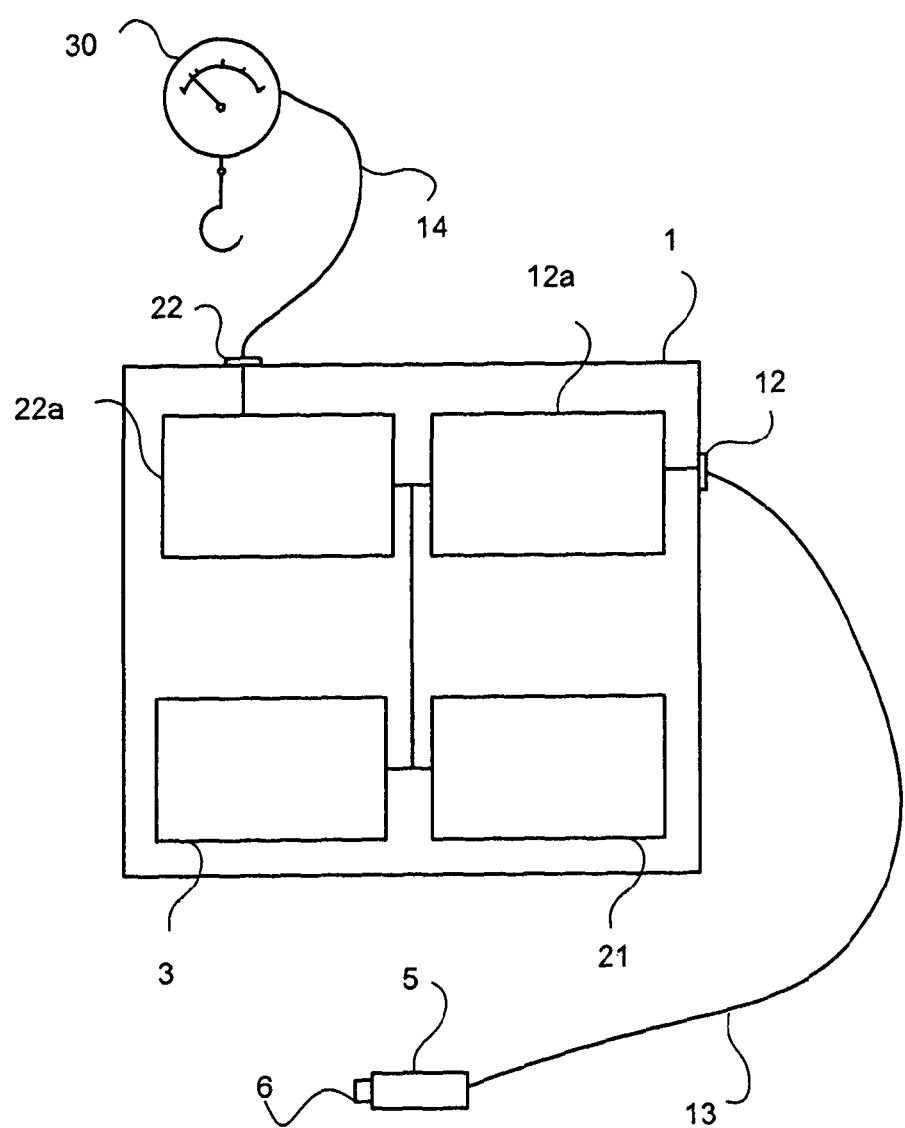
FIG. 2 is a schematic diagram showing internal components of the pump of the system of FIG. 1.

FIG. 2 shows a schematic view of the internal components of pump 1. As already mentioned, there is a control unit 3, that, among other functions mentioned later, can control how the pump 1 responds to receiving a signal from the signal input means 5. Signals from the signal input means 5 are received by the signal input device 12, 12a and are communicated to the control unit 3. The pump 1 is provided with a further input device 22, 22a. The input device 22, 22a may, for example, receive signals from a load cell 30 (which will be discussed in more detail below). The pump 1 may also comprise a memory 21, which is used to store variables, such as the settings input by a doctor or nurse to control unit 3 via the control panel 3a. Such settings can include the volume of the predetermined metered amount already mentioned. The memory 21 may also store data relating to the dispensing history of the pump 1, for example the number of times the predetermined metered amount has been dispensed in a predetermined period.

In use, the tube 2 of FIG. 1 is connected to the reservoir 4 at one end, and to the mouthpiece 11, which is provided to a patient, at the other. The patient is also provided with signal input means 5.

The nurse or authorised user may use the control panel 3a to set a predetermined metered amount of hydration fluid for oral ingestion 7 that may be provided when the signal input means 5 is operated. The volume of the predetermined metered amount will depend on factors such as the size and hydration of the patient. In the case of nil-by-mouth patients, the predetermined metered amount of hydration fluid for oral ingestion 7 is preferably not more than 20 ml, more preferably not more than 10 ml and even more preferably not more than 5 ml. The small volumes allow enough hydration fluid for oral ingestion 7 to be dispensed to the patient to wet the patient's mouth, without compromising the nil-by-mouth status of the patient. For patients who are not nil-by-mouth, the predetermined metered amount may be in the range of from 10 to 500 ml. Alternatively, for patients who are not nil-by-mouth the predetermined amount may be kept small (i.e. 20 ml or less) but the frequency of which the amounts be dispensed may be increased.

The control unit 3 may also used to set a "lock out" period of time after a predetermined metered amount has been dispensed, during which period another predetermined metered amount cannot be dispensed. This period is preferably in the range of from 1 to 30 minutes, for example 1 to 15 minutes, more preferably 2 to 10 minutes. Alternatively, the control unit may be programmed to provide the predetermined metered amount only a limited number of times in a predetermined period of time. The predetermined period of time is preferable in the range of from 30 to 90 minutes, more preferably 45 to 75 minutes, still more preferably from 55 to 65 minutes and in a preferred embodiment is 60 minutes. The limited number of times is preferably in the range of from 4 to 12, more preferably from 6 to 10, still more preferably from 7 to 9 and in a preferred embodiment is 8.

In another alternative, the control unit 3 may also be used to set a maximum value of fluid which may be dispensed in a period, for example, 100 to 800 ml per hour. If this amount of fluid has already been dispensed, the pump will not dispense any further liquid in response to user signals.

Once the pump 1 has been programmed using the control panel 3, the patient may use the signal input means to request hydration fluid for oral ingestion 7 when, for example, they are feeling especially thirsty or dehydrated. At such a time, the patient operates the signal input means 5, by pressing the button 6, to send a signal to the pump 1.

The pump 1, in response to receiving the signal via the signal input device 12, 12a may dispense the predetermined metered amount of hydration fluid for oral ingestion 7. Alternatively, if the pump has been configured with dispensing criteria (such as a limitation on the number of times a dispensing operation may take place in a certain period of time) the control unit 3 is configured to determine if the dispensing criteria are met.

If the control unit 3 determines that the dispensing criteria have been met, based on information stored in the memory 21, the pump 1 is configured to dispense the predetermined metered amount of hydration fluid for oral ingestion.

If, on the other hand, the control unit 3 determines that the dispensing criteria are not met, the pump is configured not to dispense the metered amount of hydration fluid for oral ingestion 7. In this case, the pump 1 may provide some feedback to the user to indicate that the signal has been received, but that hydration fluid for oral ingestion 7 will not be dispensed. Such a signal may be visual (for example a light, or message on a display) or auditory (for example sounding a tone or alarm). The pump 1 may be further configured to alert a person other than the user that the user is requesting more hydration fluid for oral ingestion 7 than the pump 1 is configured to dispense. This allows a doctor or nurse, for example, to review the settings which the pump 1 has been programmed with to determine whether they are still appropriate.

In the case that the dispensing criteria are met, and the pump 1 dispenses the predetermined metered amount of hydration fluid for oral ingestion 7. The pump 1 updates the dispensing history information stored in the memory 21 with information regarding the dispensing operation. When the user next sends a signal to the pump 1 via the signal input means 5 and signal input unit 12, 12a, the control unit 3 uses the updated dispensing history information to determine whether the dispensing criteria are met.

Therefore, a patient using the system 10 is able to control, within some predetermined limits, the amount of hydration fluid for oral ingestion 7 they receive, even when they are relatively incapacitated. In the embodiment described, the patient need only be able to operate the signal input means 5 which preferably comprises a button 6. It is likely that a patient will be able to operate a button 6 even when they are not able to hold a drink themselves. Further, in the case where small amounts of hydration fluid for oral ingestion 7 are being dispensed, it is easy for a patient to swallow the liquid, even if they are lying down.

Figure 3:
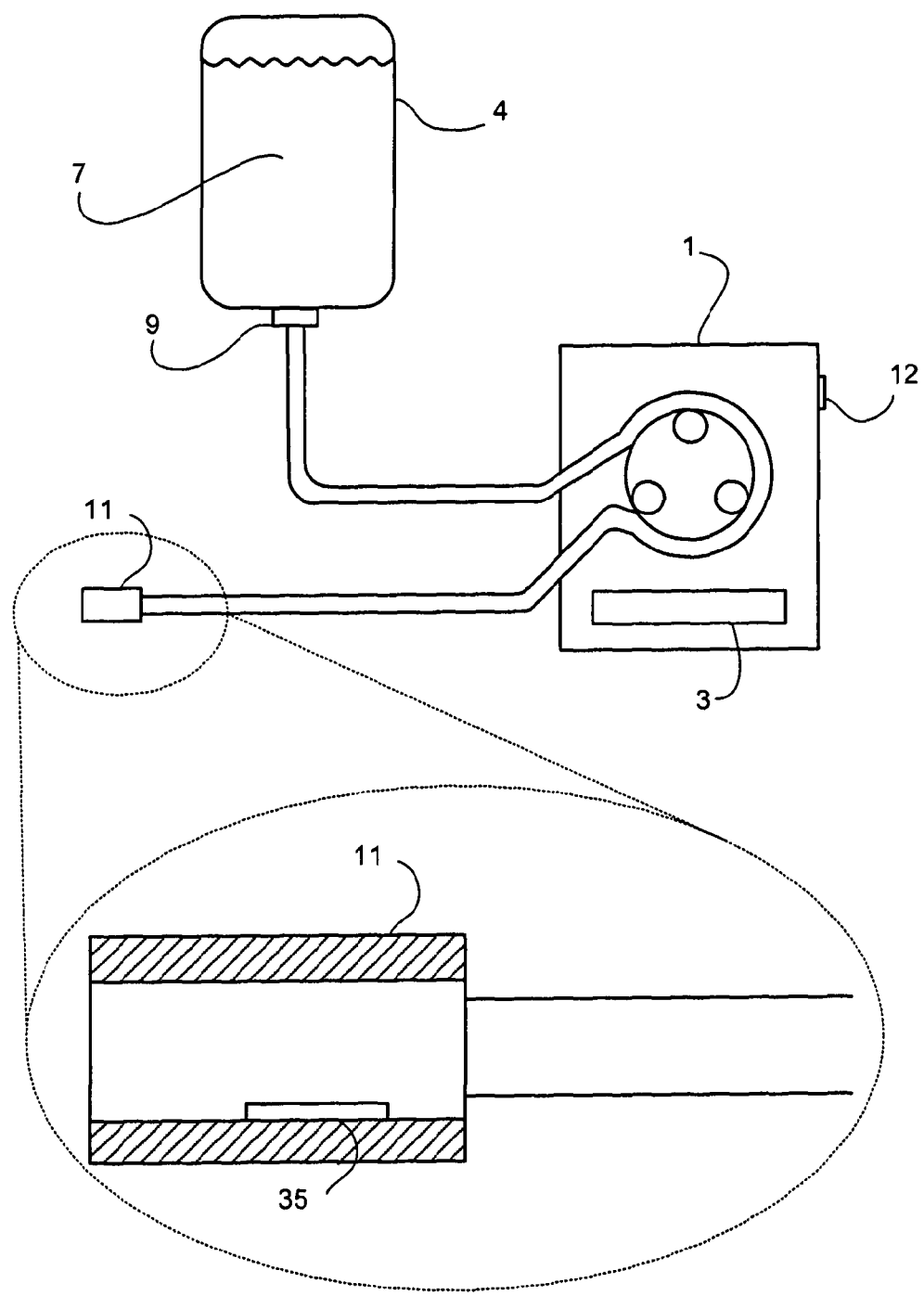
FIG. 3 is a diagram of the system of FIG. 1 showing an expanded view of the mouthpiece.

In a preferred embodiment, as shown in FIG. 3, the signal input means is incorporated into the mouthpiece which delivers the hydration fluid for oral ingestion 7 to a users mouth. As shown in the expanded and cross-sectional view of the mouthpiece 11 in FIG. 3, a signal input means 35 may be provided within the mouthpiece 11 itself. The signal input means 35 may be a switch, such as a pressure switch which is capable of detecting when a user sucks on the mouthpiece 11. Such an embodiment may be considered to be an "electronic drinking straw". Sucking on mouthpiece 11 initiates the automatic dispensing of hydration fluid 7.

In detail, when the user sucks on the mouthpiece 11, the pressure switch 35 detects that the user is sucking and sends a signal to the signal input means 12, 12a of the pump 1. The communication between the pressure switch 35 and the signal input means 12, 12a may use wired or wireless communication techniques. In the embodiment of FIG. 3, wireless communication is used between the mouthpiece 35 and the signal input means 12, 12a.

As described above, the pump 1 may or may not be programmed to use dispensing criteria to determine whether hydration fluid for oral ingestion 7 should be dispensed. If the pump 1 is not so programmed, or it is determined that the dispensing criteria are met, then the predetermined metered amount of hydration fluid for oral ingestion 7 is dispensed. As a result, the user does not need to maintain their suction on the mouthpiece 11 in order to obtain the hydration fluid for oral ingestion 7 because it is automatically dispensed. Such an embodiment is particularly preferable for infirm patients, because it makes it very easy for them to obtain hydration fluid.

If the dispensing criteria are not met, the pump 1 does not dispense any fluid, and may provide some further feedback, as discussed previously.

Figure 4:
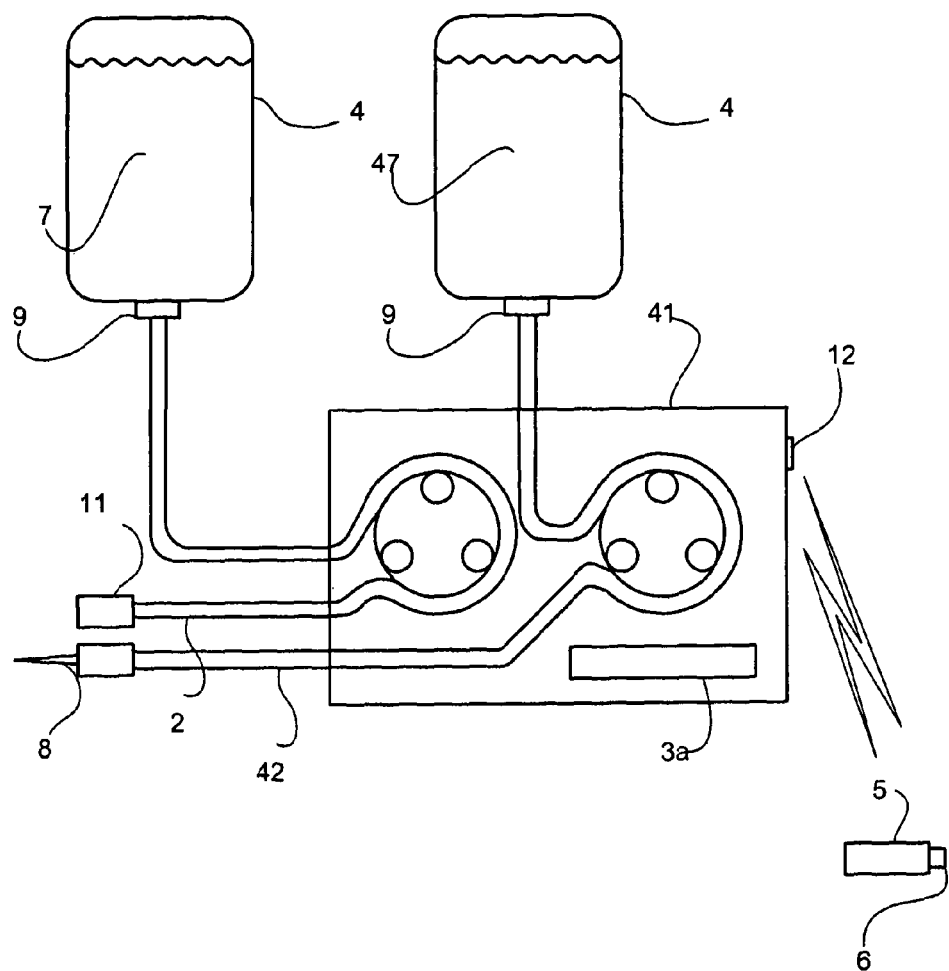
FIG. 4 is a diagram of a system for providing hydration fluids in accordance with another embodiment of the invention.

FIG. 4 shows an alternative embodiment. This embodiment incorporates the system discussed with reference to FIGS. 1-3. However, the pump 41 differs from the pump 1 of the previous embodiments in that it may dispense two different hydration fluids. The pump 41 therefore incorporates two means for providing hydration fluid, each of which may also be a peristaltic pump which forces hydration fluid through a tube 2, 42 using rollers to squeeze and release the tube 2, 42.

The second means for providing hydration fluid may be used for providing hydration fluid for intravenous delivery 47. Hydration fluids for intravenous delivery 47 may comprise or consist of crystalloids, electrolytes and/or colloids. Hydration fluid for intravenous delivery 47 may not be suitable for use as a hydration fluid for oral ingestion 7 and vice versa.

The hydration fluid for intravenous delivery 47 is provided via tube 42 from a reservoir 4. The other end of tube 42 is connected to a cannula or needle 8 which may be intravenously inserted into a patient.

The second means for providing hydration fluid may also be controlled via the control unit 3 and control panel 3a. In the case of hydration fluid for intravenous delivery 47, it may be preferable to set a base rate at which the pump 41 provides the hydration fluid for intravenous delivery 47 through the tube 42. That is, it may be preferable to set a continuous flow of hydration fluid for intravenous delivery.

The background flow rate will depend on factors such as the patient's size and how dehydrated they are. Preferably for adults the background flow rate will be in the range of from 40 to 1000 ml per hour. More preferably in the range of 50 to 500 ml per hour and even more preferably from 75 to 250 ml per hour. For small adults and children, the background flow rate may be lowered to 30 ml per hour.

The pump 41 may also be configured to provide a bolus dose of hydration fluid for intravenous delivery 47 in response to the pump 41 receiving a signal via the signal input unit 12, 12a. The pump 41 may be configured to provide hydration fluid for intravenous delivery 47 as well as or instead of the hydration fluid for oral ingestion 7 in response to receiving a signal from a user.

The bolus of hydration fluid for intravenous delivery 47 is a predetermined metered amount, and the volume of the bolus will also depend on factors such as the size and hydration of the patient. However, the volume of the bolus is preferable in the range of from 10 to 1000 ml, more preferably from 10 to 500 ml and more preferably from 100 to 300 ml.

In practice, if the pump 41 is configured to provide both a background flow of hydration fluid for intravenous delivery 47 as well as a bolus dose in response to receiving a signal from a user, the rate at which the pump 41 pumps hydration fluid for intravenous delivery 47 from the reservoir 44 through the tube 42 will increase so as to provide the bolus amount as well as the background amount of hydration fluid for intravenous delivery 47. The pumping rate used to provide the bolus is preferably in the range of from 25 to 250 ml per minute, more preferably 50 to 200 ml per minute and still more preferably 75 to 100 ml per minute.

In the case that the pump 41 is configured to dispense a bolus amount of hydration fluid for intravenous delivery 47 in response to receiving a signal from a user, the dispensing may be conditional upon the control unit 3 of the pump 41 determining that dispensing criteria have been met. The dispensing criteria may be based upon the dispensing history of the hydration fluid for intravenous delivery 47. In particular, the bolus may only be dispensed if the control unit 3 determines that the number of times the hydration fluid for intravenous delivery 47 has been dispensed in a predetermined period is less than a predetermined number of times.

The predetermined period and predetermined number of times may be different to the predetermined period and predetermined number of times used to determine whether dispensing criteria based upon the dispensing history of the hydration fluid for oral ingestion 7 are met.

The predetermined period used in the dispensing criteria concerning the dispensing history of the hydration fluid for intravenous delivery 47 is preferably in the range of from 30 to 90 minutes, more preferably from 45 to 75 minutes and still more preferably from 55 to 65 minutes and even more preferably is 60 minutes. The predetermined number of bolus doses used in the dispensing criteria based upon the history of the dispensing of the hydration fluid for intravenous delivery 47 is preferably in the range of from 1 to 5, more preferably from 1 to 3 and still more preferably is 2.

The volume of the bolus dose itself is preferably in the range of from 10 to 1000 ml, preferably from 10 to 500 ml and more preferably from 100 to 300 ml.

The pump 41 may be operated in several different modes.

In a first mode, the pump 41 may be used in a similar fashion to pump 1. That is, the pump 41 may be used to delivery only hydration fluid for oral ingestion 7. In this mode, the pump 41 dispenses hydration fluid for oral ingestion 7 in response to receiving a signal from a user and may or may not employ dispensing criteria to determine whether the hydration fluid for oral ingestion 7 should be dispensed.

In another mode, the pump 41 may be configured only to provide hydration fluid for intravenous delivery 47 as bolus doses. The bolus doses may be provided with a predetermined frequency, and/or in response to the pump 41 receiving a signal from the user. In the case that the pump 41 provides bolus doses in response to a signal from a user, the pump 41 may or may not employ dispensing criteria to determine whether the bolus dose should be dispensed.

In another mode, the pump 41 may be used to provide hydration fluid for intravenous delivery 47 as a background flow rate only. In this mode, the background flow rate is programmed into the pump 41, and does not respond to signals from a user to provide extra amounts of hydration fluid (either hydration fluid for oral ingestion 7 or hydration fluid for intravenous delivery 47).

In another mode, the pump 41 may be configured to provide hydration fluid for intravenous delivery 47 only, but using a combination of a background flow rate and bolus delivery. In this mode, the bolus delivery may be configured to be provided automatically, and/or in response to receiving a signal from a user. Once again, if the bolus delivery is in response to receiving a signal from a user, the pump 41 may employ dispensing criteria to determine whether the bolus should be dispensed.

In another mode, the pump 41 may be configured to provide a background of hydration fluid for intravenous delivery 47 and to also provide predetermined metered amounts of hydration fluid for oral ingestion 7 in response to receiving a signal from a user. The pump 41 may or may not employ dispensing criteria to determine whether a predetermined amount of hydration fluid for oral ingestion should be dispensed when receiving the signal from the user.

In another mode, the pump 41 may be configured to provide predetermined metered amounts of both the hydration fluid for oral ingestion 7 and the hydration fluid for intravenous delivery 47. The pump 41 may optionally be further configured to also provide a background flow of hydration fluid for intravenous delivery 47. The predetermined metered amount of hydration fluid for intravenous delivery 47 may be provided at a predetermined frequency or in response to a user signal. If the pump 41 is configured to dispense both the predetermined metered amounts of hydration fluid for oral ingestion 7 and the predetermined metered amounts of hydration fluid for intravenous delivery 47 in response to the same signal received from the user, separate dispensing criteria may be used to determine whether each hydration fluid should be dispensed. As a result, if there are different dispensing criteria programmed for the hydration fluid for intravenous delivery 47 and the hydration fluid for oral ingestion 7, the pump 41 may dispense either both or only one of the two hydration fluids in response to the signal from the user.

The modes which allow the dispensing of both hydration fluids 7, 47 in response to the pump 41 receiving a signal from the user are particularly effective for increasing patient hydration and also increasing patient comfort. Even when only a small amount of fluid is provided orally, providing a bolus of fluid intravenously increases patient hydration whilst the small amount of oral fluid wets the patient's mouth and increases their comfort.

In another mode, the pump 41 may be entirely controlled via external devices via input device 22, 22a.

The advantage of using the modes which provide hydration fluid for oral ingestion 7 is that this utilises the gut of the patient to absorb the fluids. Early use of the gut after an operation may help reduce morbidity, and is currently strongly advocated.

As for pump 1, the signal input means 5, 35 is not necessarily physically attached to the pump 41. The signal input means 5, 35 may be some form of remote control which communicates wirelessly with the pump 1, 41.

This has the advantage that the system does not need to be located immediately beside the patient, as long as it is in with communication range of the remote control. Suitable means for communication between a remote control signal input means 5, 35 and the pump 1, 41, via the detector 12, include, but are not limited to, infra-red, bluetooth, Wi-Fi or 3G communications.

Figure 5:
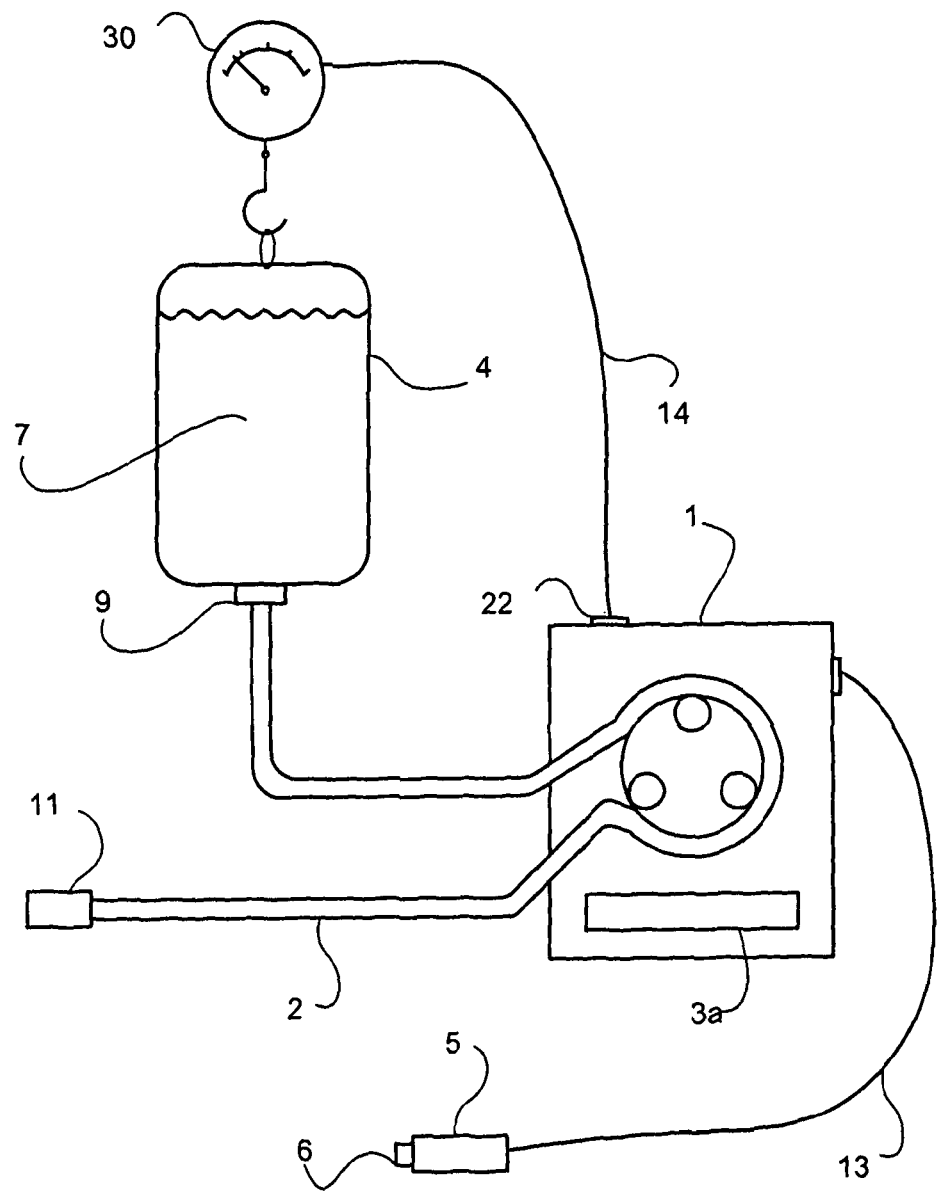
FIG. 5 is a diagram of a system for providing hydration fluids incorporating apparatus for monitoring the dispensing of the hydration fluid.

FIG. 5 shows an example of a pump 1 which embodies an apparatus for monitoring a hydration fluid dispensing process. For ease of understanding, FIG. 5 shows an apparatus based on the systems of FIGS. 1-3. However, the system of FIG. 4 may also be monitored by a similar method to that discussed below.

In FIG. 5, the reservoir 4 containing hydration fluid for oral ingestion 7 is attached to a load cell 30. The load cell 30 can therefore measure the weight of the reservoir 4 containing the hydration fluid 7. This measurement can be communicated to the pump 1 via the signal input device 22. In FIG. 5, the load cell 30 communicates with the pump 1 and communicates with input device of pump 1 via a wired connection 14, but any means of communication (including wireless communication) could be used.

According to this configuration, the control unit of pump 1 may determine the rate of change of mass of the reservoir 4 with time. This can be used to infer the rate at which the hydration fluid for oral ingestion 7 is leaving the reservoir 4. It will be readily understood that to adopt this system to the apparatus of FIG. 4, each reservoir 4 would be monitored by a separate load cell 30.

The pump 1 may be further configured to store the rate at which the pump is dispensing hydration fluid 7 at any given time in the memory 21.

The control unit 3 may be further configured to determine whether the rate stored in the memory is the same (or within a predetermined tolerance of) the rate at which it is calculated hydration fluid is leaving the reservoir 4 based on the measurements of the load cell 30. The pump 1 is further configured to provide a signal indicative of whether the rate stored in the memory 21 is the same as the rate at which fluid is calculated to be leaving the reservoir 4.

This feature of the apparatus of FIG. 5 provides a safety check to ensure that the hydration fluid 7 is being dispensed from the reservoir 4 at the correct rate. In particular, there is a known problem that when the tube 2 of a fluid giving set accidentally disengages from a peristaltic pump there is no control over the rate at which fluid leaves the reservoir 4. Typically, the reservoir 4 will be elevated with respect to the patient, and so hydration fluid 7 will flow freely from the reservoir 4 through the tube 2. This problem is known as free-flow.

The configuration of the pump in FIG. 5 allows for the detection of free-flow, because when free-flow occurs the rate at which fluid is leaving the reservoir will be measured by the load cell 30 and will differ to the rate at which the hydration fluid is intended to be dispensed by the pump 1.

The pump 1 may be configured to provide a signal indicative of whether the rate stored in the memory is the same at which fluid is measured to be leaving the reservoir 4. This may comprise providing a signal such as a light or alarm when the two rates are determined to be different, and ceasing to provide the signal when the two rates are the same. Alternatively, the opposite configuration could be used, in which a signal is provided whilst the rates are the same, and is ceased to be provided when the rates are different.

Other preferable features of the apparatuses shown in FIGS. 1-5 are discussed below.

Pumps 1, 41 are typically operated by connecting to mains power. However, the pumps 1, 41 may also be provided with a rechargeable battery so that they may continue operating in the event of a mains power failure. The pumps 1, 41 may also be provided with a small system sustain battery which will operate alarms for a minimum of 4 hours and maintain memory for a minimum of 100 days even if the rechargeable battery loses power.

Pump 41 may further be configured to provide a "Keep Vein Open" (KVO) flow rate of hydration fluid for intravenous delivery 47 whilst the cannula or needle 8 is connected to a patient. The KVO flow rate may be approximately 5 ml/hr.

Pumps 1, 41 may be further configured to determine when tubes 2, 42 become occluded. For example, sensors may detect an increase in pressure in the tubing, indicative of a blockage in the tube. Pumps 1, 41 may be further configured to reduce the pressure in the tubes 2, 42 when an occlusion is detected. Preferably, following the detection of an occlusion, the pumps 1, 41 return the tube into a neutral line pressure between 5-25 mmHg within 15 seconds, irrespective of the operating conditions. Provision of this feature is particularly preferable in the pump 41, with respect to the provision of intravenous fluids because of the greater danger to the patient when administering fluids intravenously.

Pumps 1, 41 may be further configured to receive information regarding the fluid lost by a patient. For example, a further load cell 30 connected to a urine collection bag could provide information about the fluid lost by the patient. The pumps 1, 41 may be configured to present this information to a doctor or nurse via a display, to assist them in assessing suitable parameters for patient hydration.

As previously mentioned, pumps 1, 41 may be externally programmable to provide hydration fluid. The pumps 1, 41 may incorporate safety limits, to ensure that any programmed profile or fluid delivery remains within safe boundaries. For example, the total volume may be limited to less than 2 liters of fluid per hour.

The invention claimed is:

1. An apparatus configured to dispense hydration fluid, the apparatus comprising:
a signal input device configured to receive a signal from a user,
a control unit configured to determine, in response to the signal input device receiving the signal from the user, if first dispensing criteria are met, the first dispensing criteria being based on a dispensing history of a hydration fluid for oral ingestion,
the apparatus being configured such that a predetermined metered amount of the hydration fluid for oral ingestion is dispensed if it is determined by the control unit that the first dispensing criteria are met,
wherein the control unit is further configured, in response to the signal input device receiving the signal from the user, to determine if second dispensing criteria are met; the second dispensing criteria being based on a dispensing history of a hydration fluid for intravenous delivery, and
wherein the apparatus is further configured such that a predetermined metered amount of the hydration fluid for intravenous delivery is dispensed, if it is determined that the second dispensing criteria are met.

2. The apparatus according to claim 1, wherein:
the control unit is further configured to determine how many times the predetermined metered amount of the hydration fluid for oral ingestion has been dispensed in a first predetermined period, and
wherein the control unit is configured to determine that the first dispensing criteria are met if it determines that the number of times the hydration fluid for oral ingestion has been dispensed in the first predetermined period is less than a first predetermined number of times.

3. The apparatus according to claim 1, wherein the predetermined metered amount of the hydration fluid for oral ingestion is not more than 20 ml.

4. The apparatus according to claim 1, wherein:
the control unit is further configured to determine how many times the predetermined metered amount of the hydration fluid for intravenous delivery has been dispensed in a second predetermined period, and
wherein the control unit is configured to determine that the second dispensing criteria are met if it determines that the number of times the hydration fluid for intravenous delivery has been dispensed in the second predetermined period is less than a second predetermined number of times.

5. The apparatus according to claim 1, wherein:
the control unit is further configured, in response to the signal input device receiving the signal from the user, to determine a length of time since a predetermined metered amount of the hydration fluid for oral ingestion was dispensed, and
wherein the control unit is configured to determine that the first dispensing criteria are not met if the determined length of time is less than a predefined length of time.

6. The apparatus according to claim 1, wherein:
the control unit is further configured, in response to the signal input device receiving the signal from the user, to determine a total amount of the hydration fluid for oral ingestion and the hydration fluid for intravenous delivery dispensed in a third predetermined period, and
when the control unit is configured to determine that the first dispensing criteria are not met if the total amount of the hydration fluid for oral ingestion and the hydration fluid for intravenous delivery dispensed in the third predetermined period is greater than a predetermined amount of the hydration fluid for oral ingestion and the hydration fluid for intravenous delivery.

7. The apparatus according to claim 1, wherein the apparatus is further configured to dispense a background flow of the hydration fluid for intravenous delivery.

8. The apparatus according to claim 1, the apparatus further comprising:
a mouth assembly comprising a switch, operable by the user to send the signal.

9. The apparatus according to claim 8, wherein the switch is mouth operable.

10. The apparatus according to claim 8, wherein the switch is a pressure switch.

11. The apparatus according to claim 1, wherein the predetermined metered amount of the hydration fluid for oral ingestion is not more than 10 ml.

12. The apparatus according to claim 1, wherein the predetermined metered amount of the hydration fluid for oral ingestion is not more than 5 ml.

13. A method for dispensing hydration fluid, the method comprising:
- in response to a signal from a user, determining if first dispensing criteria are met, the first dispensing criteria being based on a dispensing history of a hydration fluid for oral ingestion,
- if it is determined that the first dispensing criteria are met, dispensing a predetermined metered amount of the hydration fluid for oral ingestion,
- in response to said signal from said user, determining if second dispensing criteria are met, the second dispensing criteria being based on a dispensing history of a hydration fluid for intravenous delivery, and
- if it is determined that the second dispensing criteria are met, the method further comprises dispensing a predetermined metered amount of the hydration fluid for intravenous delivery.

14. The method according to claim 13, wherein:
- determining if the first dispensing criteria are met further comprises determining a total amount of the hydration fluid for oral ingestion and the hydration fluid for intravenous delivery dispensed in a predetermined period, and
- wherein the first dispensing criteria are not met if the total amount of the hydration fluid for oral ingestion and the hydration fluid for intravenous delivery dispensed in the predetermined period is greater than a predetermined amount of the hydration fluid for oral ingestion and the hydration fluid for intravenous delivery.

15. The method according to claim 13, the method further comprising dispensing a background flow of the hydration fluid for intravenous delivery.

16. The method according to claim 13, the method comprising:
- wherein the signal from the user is provided via a switch forming part of a mouth assembly, and the hydration fluid for oral ingestion is dispensed through the mouth assembly.

17. The method according to claim 16, wherein the switch is mouth operable.

18. A method of treating dehydration, the method comprising:
- in response to a signal from a patient, determining if first dispensing criteria are met, the first dispensing criteria being based on a dispensing history of a hydration fluid for oral ingestion,
- if it is determined that the first dispensing criteria are met, orally dispensing a predetermined metered amount of the hydration fluid for oral ingestion, to the patient
- in response to the signal from the patient, determining if second dispensing criteria are met, the second dispensing criteria being based on a dispensing history of a hydration fluid for intravenous delivery, and
- if it is determined that the second dispensing criteria are met, the method further comprises intravenously dispensing a predetermined metered amount of the hydration fluid for intravenous delivery to the patient.

* * * * *